United States Patent [19]

Mitsuhashi et al.

[11] Patent Number: 4,996,196

[45] Date of Patent: * Feb. 26, 1991

[54] NOVEL DESICCANT AND DEHYDRATION THEREWITH

[75] Inventors: Masakazu Mitsuhashi; Shuzo Sakai; Toshio Miyake, all of Okayama, Japan

[73] Assignee: Kabushiki Kaisha Hayashibara Seibutsu Kagaku Kenkyujo, Okayama, Japan

[ * ] Notice: The portion of the term of this patent subsequent to Sep. 26, 2006 has been disclaimed.

[21] Appl. No.: 382,945

[22] Filed: Jul. 21, 1989

Related U.S. Application Data

[62] Division of Ser. No. 870,132, Jun. 3, 1986, Pat. No. 4,870,059.

[30] Foreign Application Priority Data

Nov. 27, 1985 [JP] Japan ................................ 60-266559
Dec. 11, 1985 [JP] Japan ................................ 60-278634

[51] Int. Cl.$^5$ .......................... A23G 3/00; A61K 7/00; A61K 7/06; A61K 31/70

[52] U.S. Cl. ....................................... 514/53; 536/103; 424/70; 426/658; 426/442; 426/443; 514/844; 514/880

[58] Field of Search ..................... 514/53, 844, 880; 536/103; 426/658, 442, 443; 424/70

[56] References Cited

U.S. PATENT DOCUMENTS

| | | | |
|---|---|---|---|
| 3,865,957 | 2/1975 | Schieweck et al. | 426/658 |
| 3,934,048 | 1/1976 | Furda et al. | 426/548 |
| 3,953,615 | 4/1976 | Gupta et al. | 426/594 |
| 3,973,050 | 8/1976 | Hayashibara et al. | 426/552 |
| 4,102,743 | 7/1978 | Yokobayashi et al. | 435/885 |
| 4,117,173 | 9/1978 | Schiweck et al. | 426/548 |
| 4,146,706 | 3/1979 | Hitsatsuka et al. | 536/123 |
| 4,312,979 | 1/1982 | Takemoto et al. | 536/114 |
| 4,359,531 | 11/1982 | Bucke et al. | 426/536 |
| 4,386,158 | 5/1983 | Shimizu et al. | 435/178 |
| 4,556,429 | 12/1985 | Takazoe et al. | 426/658 |
| 4,572,916 | 2/1986 | Lindley et al. | 426/658 |
| 4,659,699 | 4/1987 | Francis | 536/124 |
| 4,775,749 | 10/1988 | Hijiya et al. | 424/401 |
| 4,831,022 | 5/1989 | Hijiya et al. | 424/439 |
| 4,849,225 | 7/1989 | Mitsuhashi et al. | 424/439 |
| 4,870,059 | 9/1989 | Mitsuhashi et al. | 514/53 |

FOREIGN PATENT DOCUMENTS

| | | |
|---|---|---|
| 0033549 | 2/1981 | European Pat. Off. . |
| 800324 | 7/1936 | France . |
| 448067 | 6/1936 | United Kingdom . |
| 551533 | 2/1943 | United Kingdom . |
| 1247249 | 9/1971 | United Kingdom . |
| 1293477 | 10/1972 | United Kingdom . |

OTHER PUBLICATIONS

Cereal Science Today, vol. 17, pp. 180–188 (1972).

*Primary Examiner*—Ronald W. Griffin
*Attorney, Agent, or Firm*—Browdy and Neimark

[57] ABSTRACT

There are disclosed a novel desiccant containing anhydrous maltose and dehydration of hydrous matters, e.g. food, pharmaceutical and cosmetic, therewith. Such hydrous matters are dehydrated without causing alteration or deterioration by incorporating anhydrous maltose into the hydrous matters to convert the anhydrous maltose into crystalline beta-maltose hydrate. The anhydrous maltoses usable in the invention are anhydrous crystalline alpha-maltose, anhydrous crystalline beta-maltose and anhydrous amorphous beta-maltose, specifically, those in pulverulent form.

10 Claims, 7 Drawing Sheets

NOVEL DESICCANT AND DEHYDRATION THEREWITH

This is a division of application Ser. No. 870,132 filed June 3, 1986, now U.S. Pat. No. 4,870,059.

FIELD OF THE INVENTION

The present invention relates to a desiccant and dehydration therewith.

More particularly, the present invention relates to a desiccant containing anhydrous maltose, as well as to a method for dehydrating a hydrous matter characterized by incorporating anhydrous maltose into the hydrous matter to convert the anhydrous maltose into crystalline beta-maltose hydrate.

DEFINITION

Throughout the specification, percentages and parts will be expressed by weight based on the dry solid, unless specified otherwise.

BACKGROUND OF THE INVENTION

Generally, dehydrated foods such as "ajitsuke-nori (a toasted and seasoned laver), "okaki (a dehydrated rice cake)", "okoshi (a millet-and-rice cake)" and cookie are enclosed in a moistureproof package such as a can, bottle, polyethylene-laminated aluminium foil package, and, in the moistureproof package, a desiccant such as silica gel or calcium oxide is used to decrease the atmospheric moisture and relative humidity in the moistureproof package so as to retain the quality of the dehydrated food.

Conventional desiccants, however, have the drawback that their use involves possible danger because they may come into contact with the skin or mucous surface membrane or may be misguidedly ingested. For this reason, development of a much safer desiccant has been strongly expected.

The moisture in foods greatly influences, in addition to their physical properties, their shelf lives. Generally, hydrous foods are susceptive to microbial contamination, as well as to alteration and deterioration such as hydrolysis, souring and browning.

As one means to decrease the moisture in foods to prolong their shelf lives, various dehydration methods have been employed: for example, "sato-zuke (preservation in sugar)" as in the case of "buntan-zuke (a candied citrus fruit buntan)", "shio-zuke (pickling in salt)" as in the case of "takuan-zuke (a pickled Japanese radish)", and drying method as in the case of "funmatsu-miso (powdered soybean paste)" or "funmatsu-kaju (fruit juice powder)".

However, sugar has the disadvantages that its excessive sweetness does not suit the recent preference; that the intake of sugar is a major factor of causing dental caries; and still that an excessive intake of sugar increases blood cholesterol. It has been pointed that an excessive intake of salt is one of the major causes of geriatric diseases such as hypertension and cancer. Thus, physicians advise to reduce salt intake as much as possible.

The drying method provides only insipid foods because vaporization inevitably disperses flavor during the processing steps.

Pharmaceuticals containing a bioactive substance, for example, lymphokine, hormone, vitamin, intact bacteria cell or antibiotic, are produced generally by heat-drying or lyophilizing the bioactive substance in the presence of a large amount of a stabilizer. This is because bioactive substance is unstable under high moisture conditions.

The stabilizers which have been used are water-soluble polymers such as albumin, casein, gelatin and hydroxylethyl starch.

Dehydration in the presence of these water-soluble polymers, however, has the demerits that it consumes a relatively large amount of energy: that it may insolubilize the final product; and still that it may inactivate bioactive substances.

SUMMARY OF THE INVENTION

In view of the foregoing, we have investigated the use of maltose in a desiccant which overcomes these drawbacks of the conventional dehydration methods.

As the result, we found that anhydrous maltose, specifically, anhydrous crystalline maltose with a maltose content of 85% or higher, acts as a strong desiccant when incorporated into hydrous matters, such as those of foods and pharmaceuticals, to effect conversion into crystalline betamaltose hydrate; as well as that tasty and high-quality dehydrated foods and stable and highly-active pharmaceuticals can be easily prepared in this way.

BRIEF DESCRIPTION OF THE ACCOMPANYING DRAWINGS

DESCRIPTION OF THE PREFERRED EMBODIMENTS

Figure 1:
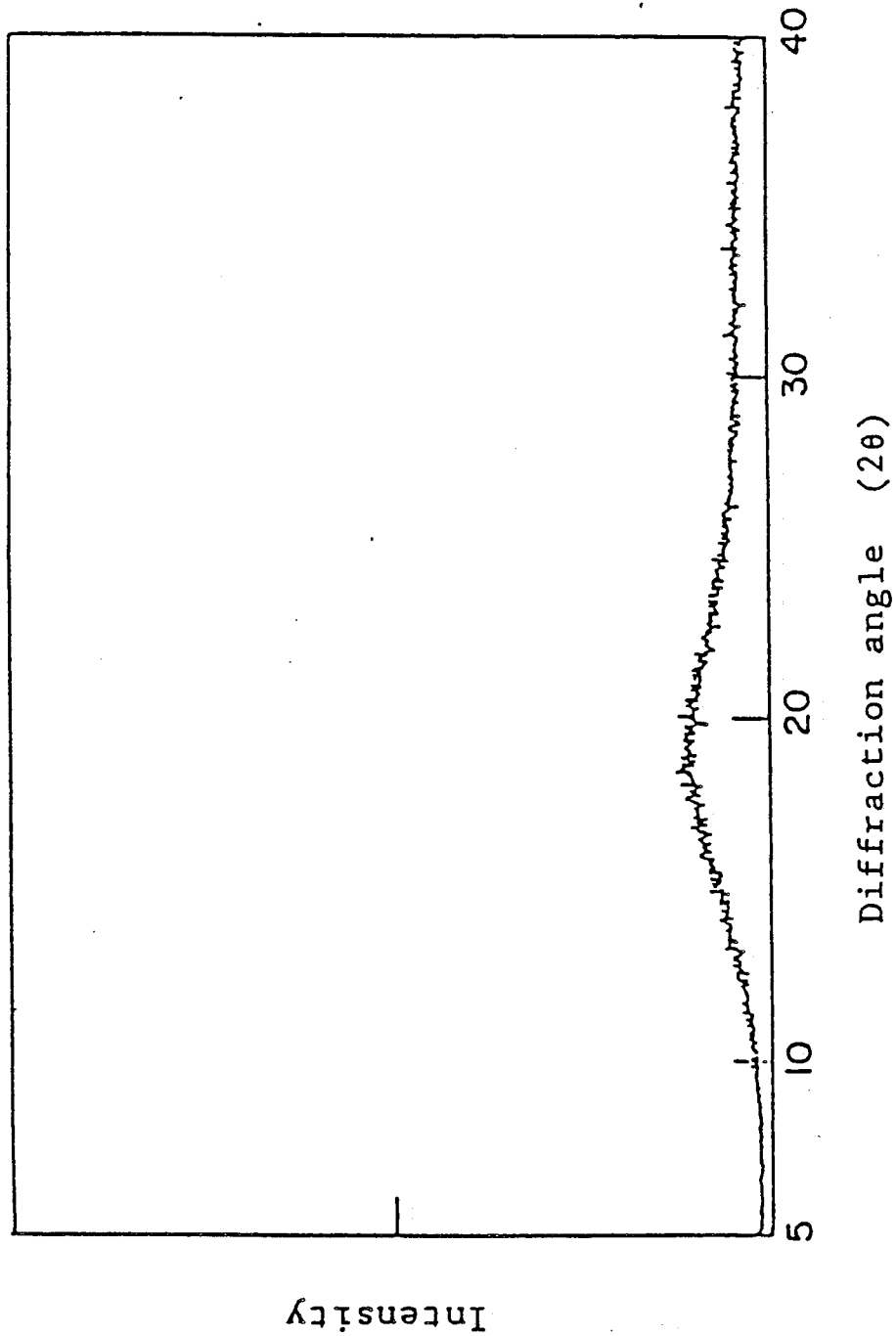
FIG. 1 is the x-ray diffraction figure of an amorphous powder with an alpha-maltose content of 48.0%.

The present invention utilizes anhydrous maltose which has drawn no attention as possible desiccant. The present invention is the first instance where a hydrous matter is dehydrated by incorporation of anhydrous maltose.

The dehydration method according to the invention is advantageous for dehydration of a matter which has a free moisture content but not of a binding water such as water of crystal. For example the present invention can be advantageously used to dehumidify a moistureproof package wherein a dehydrated food is enclosed, as well as to reduce the moisture in various hydrous matters, for example, those of foods, pharmaceuticals, cosmetics, chemicals, and their materials and intermediates.

We found that incorporation of anhydrous maltose strongly entraps about 5 w/w % of moisture from a hydrous matter to substantially eliminate its moisture or even to bring it to dryness.

Also was found that the relative humidity in a moistureproof package enclosing a dehydrated food, for example, "ajitsuke-nori" or cookie, is extremely decreased by placing anhydrous maltose packed in a small moisture-permeable paper bag in the moistureproof package, whereby the quality of the dehydrated product is stably retained over a long period of time.

Since anhydrous maltose neither becomes sticky nor gutters during or after conversion into crystalline beta-maltose hydrate, moistureproof package and dehydrated food have no fear of staining.

In addition, the practice of the present invention leads to no harm because maltose per se is a non-toxic and harmless natural sweetener.

According to the invention, a high-quality food with a substantially-decreased moisture in the form of, for example, massecuite or powder, can be easily prepared by dehydrating a high-moisture content food in liquid or paste form, for example, brandy, vinegar, royal jelly, fresh cream and mayonnaise. This method has the feature that such a high-moisture content food is easily converted into a tasty dehydrated form without causing alteration and deterioration because this method uses no vigorous processing step such as heat-drying.

We found that the inner space of a moistureproof package can be kept at highly-desiccated conditions by adding anhydrous maltose in an amount over the moisture in the hydrous food material to be enclosed therein to obtain a dehydrated food wherein the anhydrous maltose is partially converted into crystalline beta-maltose hydrate, i.e. a dehydrated food containing both anhydrous maltose and beta-maltose hydrate; and enclosing the dehydrated food in the moistureproof package so as to entrap the moisture in the package with the remaining anhydrous maltose. This decreases the relative humidity in the moistureproof package.

Also was found that, as a consequence, the present invention prevents alteration and deterioration such as microbial contamination, hydrolysis, souring or browning in dehydrated foods; and still that the obtained tasty foods retain their quality over a long period of time.

In the case of an aqueous solution of lymphokine or antibiotic, or a paste of pharmaceutical such as ginseng extract or snapping turtle extract, a high-quality pharmaceutical with a substantially decreased moisture in, for example, massecuite or powder can be easily prepared by incorporating anhydrous maltose into the aqueous solution or paste to convert the anhydrous maltose into crystalline beta-maltose hydrate.

This method provides a high-quality and stable pharmaceutical because the method uses no vigorous processing step such as heat-drying and also because anhydrous maltose acts as a stabilizer.

Conventional stabilizer such as water-soluble polymer can be suitably used to obtain a much more stabilized pharmaceutical without wasting energy for dehydration of the stabilizer.

The present invention can be advantageously practiced in the preparation of solid injection by, for example, placing a prescribed amount of anhydrous maltose in a vial; adding to the vial an aqueous solution containing a bioactive substance, for example, lymphokine or hormone, in an amount below the moisture that is required to convert completely the anhydrous maltose; and sealing the the vial.

We found that, in such case, anhydrous maltose dehumidifies the inside air of the vial, as well as dehydrating the aqueous solution.

Also was found that, as a consequence, the present invention facilitates the preparation of dehydrated pharmaceuticals; and still that the obtained pharmaceuticals retain their high quality over a long period of time and readily dissolve in water on use.

As described above, unlike conventional desiccant such as silica gel and calcium oxide, the desiccant using anhydrous maltose has the advantages that it is an edible saccharide and, therefore, assimilable and alimentary in the body; and that it acts as the stabilizer bioactive substances.

We have investigated preparation of anhydrous maltose, specifically, anhydrous maltose powder.

We have investigated in detail the use of anhydrous maltose as desiccant. As the result, we found that a high-purity maltose with a maltose content of 85% or higher is suitable for desiccant.

The high-purity maltose used in anhydrous maltose preparation is a commercialized crystalline beta-maltose hydrate, or that obtained by saccharifying starch in conventional manner.

Examples of the method to prepare a high-purity maltose from starch is that as disclosed in Japan Patent Publication Nos. 11,437/81 and 17,078/81 wherein a gelatinizedor liquefied-starch is subjected to the action of beta-amylase to form maltose which is then separated from maltodextrins; and that as disclosed in Japan Patent Publication Nos. 13.089/72 and 3,983/79 wherein a gelatinized- or liquefied-starch is subjected to a starch-debranching enzyme, for example, isoamylase or pullulanase, and beta-amylase.

Other saccharides, for example, maltotriose, present in the obtained high-purity maltose may be further subjected to the action of an enzyme, for example, as disclosed in Japan Patent Publication Nos. 28,153/81, 3,356/82 and 28,154/81, to hydrolyze into maltose; or, as disclosed, for example, in Japan Patent Kokai No. 23,799/83, removed by fractionation using a column of a strongly-acidic cation exchange resin to increase the maltose content. Such fractionation can be carried out by the fixed bed-, moving bed-, or simulating moving bed-method.

The following explains the preparation of anhydrous maltose from the high-purity maltose with a maltose content of 85% or higher.

Examples of the anhydrous maltose are anhydrous crystalline alpha-maltose, crystalline beta-maltose, and anhydrous amorphous maltose.

As disclosed, for example, in Japan Patent Kokai No. 35,800/86, a pulverulent anhydrous crystalline alpha-maltose is produced by preparing a high-purity maltose into a syrup with a moisture content of less than about 10 w/w %, desirably, 2.0 w/w % or higher but lower than 9.5 w/w %; retaining the syrup at 50°–130° C. in the presence of seed to effect crystallization; and pulverizing the resultant anhydrous crystalline alpha-maltose.

The method that is used to prepare an anhydrous crystalline beta-maltose hydrate powder is, for example, a method wherein vacuum drying is effected under conditions, for example, in the temperature range of about 80°–110° C., that do not melt crystalline beta-maltose hydrate powder.

Anhydrous amorphous maltose powder can be prepared from, for example, a commercialized crystalline beta-maltose hydrate, or an aqueous solution of a high-purity maltose with a maltose content of 85% or higher.

When a commercialized crystalline beta-maltose hydrate is used, an anhydrous amorphous maltose powder can be prepared by dehydrating the beta-maltose hydrate at either ambient- or relatively high-pressure and at a temperature in the range of, for example, about 120°–150° C. that melts the beta-maltose hydrate When an aqueous solution is used, the objective powder can be directly prepared by vacuum drying or lyophilization of a syrup having a concentration of about 70–95%, and either pulverizing the resultant product; or spray-drying about 50–85% syrup with a high-pressure nozzle or a rotary disc.

The anhydrous maltose thus obtained is a white powder with a mild reduced sweetness. The moisture of the anhydrous maltose is extremely low or substantially anhydrous: The Karl Fischer's method gave a moisture content, generally, below 3 w/w %, desirably, a moisture content of below 2 w/w %. The anhydrous maltose is substantially free-flowing, but this slightly varies dependently on the particle shape and size.

The wording "anhydrous maltose" shall mean substantially-anhydrous maltose that is convertible into crystalline beta-maltose hydrate while exhibiting a strong dehydrating activity. In order to accelerate the conversion to increase the activity, for example, it is advantageous to use a minimum amount of a substantially-anhydrous amorphous maltose powder that contains crystalline beta-maltose hydrate, generally, less than 5%, desirably, less than 1%.

We found that incorporation of an anhydrous maltose powder into a hydrous matter, for example, food, pharmaceutical, cosmetic or chemical, entraps the moisture in the matter as the water of crystal to form crystalline beta-maltose hydrate. Thus, the anhydrous maltose powder acts as strong desiccant on the hydrous matter.

Also was found that anhydrous maltose, unlike commercialized crystalline beta-maltose hydrates, for example, "SUNMALT ®", a product of Hayashibara Co., Ltd., Okayama, Japan, readily dissolves, as well as in water, in an aqueous solution of organic acid, salt, protein or alcohol, and emulsion to give a high maltose concentration. This is very advantageous for utilizing anhydrous maltose as the desiccant to prepare various moisture-decreased products from hydrous matters.

The desiccant according to the invention can be advantageously used when moistureproof package must be dehumidified and/or dehydrated, and when a high-quality dehydrated product in massecuite or powder form is prepared from a hydrous matter that is susceptive to alteration and/or deterioration during heat- or vacuum-drying.

The present desiccant is specifically advantageous when the hydrous products are those of origins such as animal, plant or microorganism, such as organ, tissue, cell, triturate, extract component, and preparations obtained therefrom.

When the hydrous matter is a food, or its material or intermediate in liquid or paste form, a stable and tasty dehydrated food can be easily prepared according to the invention. Examples of such hydrous matter are agricultural products such as fresh fruit, juice, vegetable extract, soybean milk, sesame paste, nut paste, "nama-an (unsweetened bean jam)", gelatinized starch paste and flour dough; marine products such as sea urchin paste, oyster paste and sardine paste; poultry products such as fresh egg, lecithin, milk, whey, fresh cream, yogurt, butter and cheese; hydrous seasonings such as maple syrup, honey, "miso (soybean paste)", soy sauce, mayonnaise, dressing, bonito extract, meat extract, tangle extract, chicken extract, beef extract, yeast extract, mushroom extract, licorice extract, stevia extract, enzymatically processed product thereof and seasoning liquid for pickles; liquors such as Japanese sake, wine, brandy and whisky; soft drinks such as tea, green tea and coffee: hydrous spices such as those extracted from peppermint, "wasabi (Japanese horseradish)", garlic, mustard, "sansho (Japanese pepper tree)", cinnamon, sage, laurel, pepper, and citrus fruits; and hydrous coloring agents such as those extracted from madder, turmeric, paprika, red beet, safflower, cape jasmine, saffron, sorghum and Monascus microorganism.

The dehydrated products obtained in this way, for example, powdered agricultural- or poultry-product, powdered oil and fat, flavor powder and coloring agent powder can be conveniently used, for example, as a natural bulk flavor excellent in taste and flavor, in various foods, for example, seasonings such as mayonnaise and soup stock; confectioneries such as hard candy and cake; and instant foods such as hot cake mix and instant juice.

When the hydrous matter is a pharmaceutical, or its material or intermediate, a stable and highly-active pharmaceutical can be easily prepared according to the invention without inactivating the effective ingredients. Examples of such hydrous matter are a solution containing lymphokine such as interferon, lymphotoxin, tumor necrosis factor, macrophage migration inhibitory factor, colony-stimulating factor, transfer factor or interleukin 2; a solution containing hormone such as insulin, growth hormone, prolactin, erythropoietin or follicle-stimulating hormone: a solution containing a biological such as BCG vaccine, Japanese encephalitis vaccine, tetanus toxoid, Trimeresurus antitoxin or human immunoglobulin; a solution containing antibiotic such as penicillin, erythromycin, chloramphenicol, tetracycline, streptomycin or kanamycin sulfate; a solution containing a vitamin such as thiamine, riboflavin, ascorbic acid, liver oil, carotenoid, ergosterol or tocopherol; a solution containing an enzyme such as lipase, elastase, urokinase, protease, beta-amylase, isoamylase, glucanase or lactase; an extract such as ginseng extract, snapping turtle extract, chlorella extract or aloe extract; and cell paste such as that of lactic acid bacterium or yeast.

When the hydrous matter is a cosmetic, or its material or intermediate, a high-quality cosmetic can be easily prepared by dehydrating a hydrous matter such as fresh egg, lecithin, fresh cream, honey, licorice extract, flavor, coloring agent or enzyme similarly as in the case of foods or pharmaceuticals. The resultant product can be advantageously used as skin- and hair-treatments, and hair tonic.

When the hydrous matter is an enzyme, the resultant product can be advantageously used in the catalyst for preparing foods, pharmaceuticals and chemicals, as well as in therapeutic, digestive and detergent.

Anhydrous maltose is incorporated into a hydrous matter, for example, by mixing, kneading, dissolving, permeating, sprinkling, coating, spraying or injecting before the processing steps are over.

The amount of anhydrous maltose to be incorporated is, generally, against one part of a hydrous matter, 0.01–500 parts, desirably, 0.1–100 parts, but varies with the properties of the final product. To improve further the quality of the resultant product, one or more of flavor, coloring agent, seasoning, stabilizer and filler can be used along with anhydrous maltose.

Such stabilizer may be a water-soluble polymer that has been deemed hardly dehydratable, and is not limited to a low-molecular weight compound such as conventional antioxidant because even such water-soluble polymer is strongly dehydrated with anhydrous maltose. For this reason, water-soluble polymers, for example, soluble starch, dextrin, cyclodextrin, pullulan, elsinan, dextran, xanthan gum, gum arabic, locust bean gum, guar gum, tragacanth gum, tamarind gum, carboxymethyl cellulose, hydroxyethyl cellulose, hydroxyethyl starch, pectin, agar, gelatin, alubumin and casein can be advantageously used as the stabilizer.

When such water-soluble polymer is used, a dehydrated food with microcrystals of beta-maltose hydrate can be prepared first by homogenously dissolving a water-soluble polymer in a hydrous product in, for example, liquid or paste form; then incorporating anhydrous maltose homogenously into the resultant solution with a suitable procedure such as mixing or kneading. In the resultant food, the flavor- and effective-components are coated with a membrane of the water-soluble polymer, or enclosed together with the beta-maltose hydrate microcrystals in a microcapsule of the membrane. When cyclodextrin is used in combination with anhydrous maltose, dispersion, alteration and/or deterioration of the above described components is prevented by formation of inclusion complexes. For this reason, this method superiorly retains the flavor- and effective-components that are present in hydrous matters.

In the present invention, various procedures can be used for preparing dehydrated products, specifically, those in pulverulent form. For example, anhydrous maltose is incorporated homogenously into a hydrous matter, such as food, pharmaceutical, chemical, or their material or intermediate, with a relatively high moisture to give a moisture content of about 30 w/w % or lower, desirably, about 5-25 w/w %, and the resultant mixture is allowed to stand at a temperature of about 10°-50° C., for example, ambient temperature, for about 1-10 days to convert the anhydrous maltose into beta-maltose hydrate to obtain a block which is then pulverized by scraping, cutting or crushing. If necessary, drying- and sieving-steps may follow the pulverization.

Spraying method directly provides such powder. For example, a prescribed amount of a hydrous matter in liquid or paste form is sprayed towards a fluidizing anhydrous maltose to effect granulation, and then aged at about 30°-60° C. for about 1-24 hours to convert the anhydrous maltose into crystalline beta-maltose hydrate. Alternatively, a powder obtained by mixing or kneading anhydrous maltose with a hydrous matter in liquid or paste, and, immediately or after starting the conversion, spraying the resultant mixture is aged similarly. These methods are favorable for preparing pulverulent product on a large scale.

The spraying method can be advantageously practiced by using a minimum amount of crystalline beta-maltose hydrate to accelerate the conversion and to shorten the subsequent ageing.

The powder obtained in this way can be shaped into any form, for example, granule, tablet, capsule, rod, plate or cube, alone or, if necessary, in combination with filler, vehicle, binder and/or stabilizer, prior to its use.

The present invention can be advantageously practiced in the preparation of a saccharide-coated product by coating a suitable center, for example, food such as peanut, almond or candy, or pharmaceutical intermediate such as granule or tablet, with an about 70-95% aqueous solution of anhydrous maltose, desirably, that additionally contains an appropriate amount of a binder such as water-soluble polymer to cover or coat the center.

Incorporation of anhydrous maltose into a high-moisture content matter by mixing or kneading swells the matter as the conversion and dehydration proceed. When swelling occurs vigorously, the resultant product increases its volume 1.5- to 4.0-folds. The product that has been solidified with swelling has the feature that it can be easily pulverized with a less abrasion of scraper, cutter or pulverizer and a less electric consumption therefor because such product is softer than that with a less swelling.

This phenomenon is utilizable in the preparation of dehydrated food of a desirable form. For example, a dehydrated product in the shape of, for example, flower, bird, fish or doll can be prepared by placing a high-moisture content matter which has been incorporated with anhydrous maltose in a plastic casting vessel; and allowing the high-moisture content matter to stand at ambient temperature for about 5-90 hours to effect swelling and solidification. To accelerate the swelling, a volatile solvent such as alcohol or an agent that forms carbonic acid gas can be incorporated together with anhydrous maltose, and then heated at a briefly, if necessary. In order to accelerate the conversion into crystalline beta-maltose hydrate and to shorten the conversion time, anhydrous maltose may be exposed to a vaporous atmosphere.

The shaped products obtained in this way can be advantageously used, for example, for foods such as confectioneries, cosmetics and pharmaceuticals.

Generally, starch requires a relatively large amount of moisture in its swelling and gelatinization. For this reason, gelatinized starch is susceptive to microbial contamination. Anhydrous maltose can be advantageously used to dehydrate gelatinized starch. For example, microbial contamination of a gelatinized starch product such as "gyuhi (a rice paste)" can be prevented by incorporating anhydrous maltose to convert it into crystalline beta-maltose hydrate and to decrease the moisture in the product.

Furthermore, incorporation of anhydrous maltose extremely prolongs the shelf lives of processed foods that contain gelatinized starch because anhydrous maltose disperses homogenously in the gelatinized starch and acts as the agent that prevents retrogradation.

Crystalline alpha-maltose can be advantageously used as the antiseptic or stabilizer for foods, or agent for improving their quality because, in the case of a high-moisture content solid food, for example, peeled banana, peeled orange, slices of steamed sweet potato, opened and dried saurel, rawor steamed-noodle or rice cake, that is susceptible to microbial contamination, crystalline alpha-maltose forms a coating of crystalline beta-maltose powder on the surface of the solid food to decrease its surface moisture, as well as improving the shelf life and quality of the solid food. In such case, anhydrous maltose may be used in combination, for example, with lactic acid, citric acid or ethanol, to further prolong the shelf life of the solid food.

Anhydrous maltose exhibits a high affinity to alcohols. Because of this property, anhydrous maltose can be advantageously used as the desiccant for alcohols and alcohol-soluble matters, such as methanol, ethanol, butanol, propylene glycol and polyethylene glycol. For example, a dehydrated liquor in massecuite or powder can be prepared by dehydrating a liquor such as Japanese sake, "shochu (a Japanese distilled spirits)", wine, brandy, whisky or vodka; their effective component and flavor being retained in the resultant crystalline beta-maltose hydrate. The obtained liquor powder can be used in confectioneries and premixes, as well as in beverages after dissolution in water.

In the above case, anhydrous maltose imparts a mild sweetness, body and appropriate viscosity to the liquor, as well as dehydrating and stabilizing the liquor.

The present invention can be advantageously practiced in the preparation of ointments in massecuite form with an appropriate viscosity, spreading rate and adhesiveness that stably retain their effective element such as iodine by mixing an alcoholic solution of iodine with anhydrous maltose, and adding an aqueous solution containing a water-soluble polymer to the resultant mixture to convert the anhydrous maltose into crystalline beta-maltose hydrate.

Anhydrous maltose exhibits an unexpectedly high affinity to oil and fat though it is a hydrophilic saccharide.

Because of this property, anhydrous maltose can be advantageously used as the desiccant for oil-soluble substance, emulsion or latex, specifically, as the desiccant that entraps a trace moisture in oil-soluble substances. Examples of such oil-soluble substances are fats and oils such as soybean oil, rapeseed oil, mustard oil, sesame oil, safflower oil, palm oil, cacao butter, beef tallow, lard, chicken oil, marine oil and hardened oil; oil-soluble spices such as citrus essential oil, flower essential oil, spice oil, peppermint oil, spearmint oil, cola nut extract and coffee extract; oil-soluble coloring agent such as beta-carotin, paprika pigment, annotto pigment and chlorophyll; oil-soluble vitamins such as liver oil, vitamin A, vitamin $B_2$ lactate, vitamin E, vitamin K and vitamin D; oil-soluble hormones such as estrogen, progesterone and androgen; and unsaturated higher fatty acids such as linoleic acid, linolenic acid, arachidonic acid, eicosapentaenoic acid and docosahexaenoic acid.

The resultant dehydrated oil-soluble substances is featured by the high-quality and low susceptivity to alteration and deterioration such as hydrolysis and souring.

This method can be advantageously practiced in the preparation of pulverulent foods such as those of oil and fat, spice, flavor and coloring agent, pulverulent cosmetics, and pulverulent pharmaceuticals such as those of vitamin and hormone by impregnating or mixing an oil-soluble substance in anhydrous maltose.

In this case, anhydrous maltose acts as the desiccant, as well as a stabilizer, retainer, vehicle and carrier.

Anhydrous maltose can be advantageously used in foods containing oil-soluble substance, such as chocolate and cream filling, where the presence of moisture is undesirable. In this case, in addition to the dehydrating activity, the properties of anhydrous maltose to improve processibility, melting properties and flavor are utilized. The obtained products are characterized in retaining their high-quality over a long period of time.

As described above, the present invention is based on the finding that anhydrous maltose strongly dehydrates various hydrous matters. By using anhydrous maltose as the desiccant, foods, cosmetics and pharmaceuticals that have a decreased moisture and high-quality can be prepared from a hydrous matter in liquid or paste form without causing, in foods and cosmetics, deterioration and/or dispersion of taste and flavor, and, in pharmaceuticals, decomposition and/or inactivation of their effective components.

In addition to the above mentioned special uses, anhydrous maltose can be advantageously used in the preparation of foods, pharmaceuticals and cosmetics because anhydrous maltose is a natural sweetener and has the inherent feature of maltose that it imparts a mild sweetness, body, texture, viscosity and moisture-retaining properties to these matters without fear of increasing their cariogenicty and blood cholesterol.

Anhydrous maltose is an assimirable nutrient; this property is inherent to maltose.

When anhydrous maltose is parenterally used in the form of, for example, injection, anhydrous maltose supplies 2-fold higher calorie than glucose because in solution maltose becomes isotonic when used in 2-fold higher concentration. For this reason, anhydrous maltose is suitable for hyperalimentation when, as in the case of a surgical operation, the subject requires a relatively high calorie supplement.

The following is illustrative of additional uses of the present desiccant.

Anhydrous maltose can be used as the sweetener with a strong dehydrating activity.

Anhydrous maltose can be used along with one or more sweeteners, for example, powdered syrup, glucose, isomerized sugar, sucrose, honey, maple sugar, sorbitol, maltitol, dihydrocharcone, stevioside, alpha-glycosyl stevioside, sweet substance derived from *Momordica grosvenori* Swingle, glycyrrhizin, thaumatin, L-asparatyl L-phenylalanine methyl ester, saccharin, glycine or alanine; and/or filler such as dextrin, starch or lactose.

Since anhydrous maltose has the features that it has the inherent mild sweetness of maltose; that it well harmonizes with the sour-, acid-, salty-, astringent-, bitter- and delicious-tastes of other substances: and that it is highly acidand heat-resistant, anhydrous maltose can be freely used for dehydrating foods in general, as well as for sweetening or improving their taste quality.

Examples of the foods are seasonings such as soy sauce, powdered soy sauce, "miso", "funmatsu-miso (powdered miso)", "moromi (an unrefined sake)", "hishio (a refined soy sauce)", "furikake (a seasoned fish meal)", mayonnaise, dressing, vinegar, "sanbai-zu (a sauce of sauce, soy, and vinegar)", "funmatsu-sushi-no-moto (a premix for seasoning sushi)", "chuka-no-moto (an instant mix of Chinese dish)", "tentsuyu (a sauce for Japanese deep-fat fried food)", "mentsuyu (a sauce for Japanese vermicelli)", sauce, catsup, "yakiniku-no-tare (a sauce for Japanese grilled meat)", curry roux, instant stew mix, instant soup mix, "dashi-no-moto (an instant stock mix)", mixed seasoning, "mirin (a sweet sake)", "shin-mirin (a synthetic mirin)", table sugar and coffee sugar.

Also, anhydrous maltose can be freely used for dehydrating "wagashi (Japanese cakes)" such as "senbei (rice crackers)", "arare-mochi (pellet-shaped senbei)", "okoshi (a millet-and-rice cake)", "gyuhi (a rice paste)", rice paste, "manju (a bun with a bean-jam filling)", "uiro (a sweet rice jelly)", "an (a bean jam)", "yokan (a sweet jelly of beans)", "mizu-yokan (a soft adzuki-bean jelly)", "kingyoku (a kind of yokan)", jelly, pao de Castella (a sponge cake) and "amedama (toffees)"; confectioneries and bakery products such as bun, biscuit, cracker, cookie, pie, pudding, butter cream, custard cream, cream puff, waffle, sponge cake, doughnut, chocolate, chewing gum, caramel and candy; frozen desserts such as ice cream and shurbet; syrups such as "kajitsu-no-syrup-zuke (a preserved fruit)" and "korimitsu (a sugar syrup for shaved ice)"; pastes such as flour paste, peanut paste and fruit paste; processed fruits and vegetables such as jam, marmalade, "syrup-zuke (fruit pickles)" and "toka (conserves)"; pickles and pickled products such as "fukujin-zuke (red colored radish pickles)", "bettara-zuke (a kind of whole fresh radish pickles)", "senmai-zuke (a kind of sliced fresh radish pickles)" and "rakkyo-zuke (pickled shallots)"; premixes for pickles and pickled products such as "takuan-zuke-no-moto (a premix for pickled radish)" and "hakusai-zuke-no-moto (a premix for fresh white rape pickles)"; meat products such as ham and sausage; fish meat products such as fish ham, fish sausage, "kamaboko (a steamed fish paste)", "chikuwa (literally bamboo wheels)" and "tenpura (a Japanese deep-fat fried fish paste)"; "chinmi (relish)" such as "uni-no-shiokara (salted guts of sea urchin)", "ika-no-shiokara (salted guts of squid)", "su-konbu (a processed tangle)", "saki-surume (dried squid strips)" and "fugu-no-mirinboshi (a dried mirin-seasoned swellfish)"; "tsukudani (foods boiled down in soy)" such as those of laver, edible wild plants, dried squid, fish and shellfish; daily dishes such as "nimame (cooked beans)", potato salad and "konbu-maki (a tangle roll)"; milk products; canned and bottled products such as those of meat, fish meat, fruit and vegetable; alcoholic beverages such as synthetic sake, "zozyo-shu", fruit wine and liquors; soft drinks such as coffee, cocoa, juice, carbonated beverage, sour milk beverage and beverage containing a lactic bacterium; instant foodstuffs such as instant pudding mix, instant hot cake mix, juice powder, instant coffee, "sokuseki-shiruko (an instant mix of adzuki-bean soup with rice cake)" and instant soup mix, as well as for sweetening and improving their taste quality.

Anhydrous maltose can be used in animal feeds and pet foods directed to domestic animal and fowl, pet animal, fish, honey bee, silkworm, and fish for dehydrating and improving their taste quality.

In addition, anhydrous maltose can be freely used to sweeten tobaccos, cosmetics and pharmaceuticals in solid, paste or liquid form, such as cigar, cigarette, dentifrice, lipstick, lipcream, medicine for internal administration, troche, liver oil drop, oral refreshing agent, cachou and collutorium, as well as to improve their taste quality.

The following experiments will explain the present invention in more detail.

EXPERIMENT 1

Comparison of material maltose

Several starch sugar products as listed in Table I, commercialized by Hayashibara Co., Ltd., Okayama, Japan, were used as the material maltose. The syrup product, i.e. "MALSTAR®" or "HM-75", was charged in an evaporator and evaporated in vacuo to give a moisture content of 4.5 w/w %.

The crystalline beta-maltose hydrate powder, i.e. "SUNMALT®", "MALTOSE H", "MALTOSE HH" or "MALTOSE HHH", was dissolved with a small amount of water by heating, charged in an evaporator, and evaporated in vacuo to give a moisture content of 4.5 w/w %.

Figure 2:
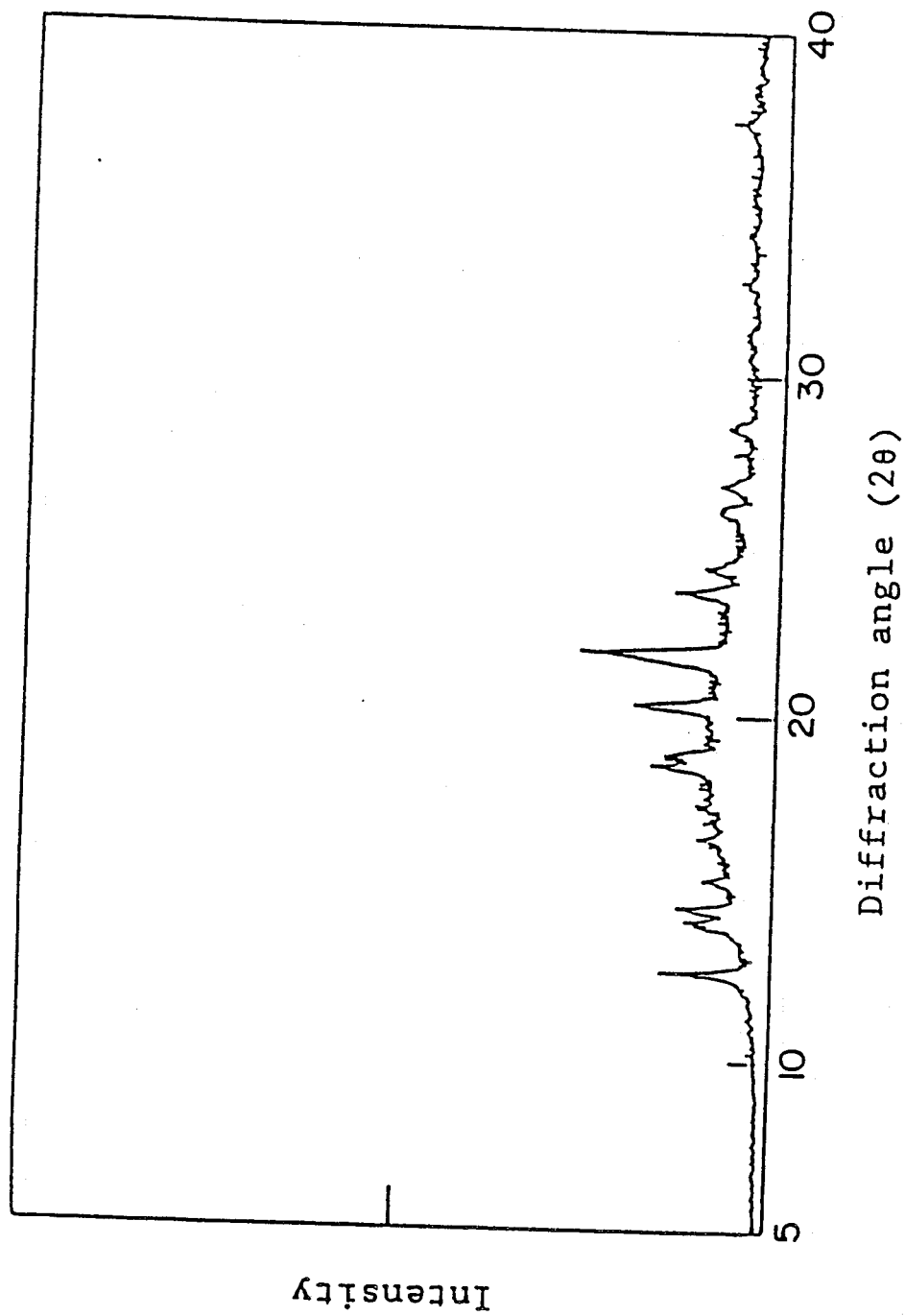
FIG. 2 is the x-ray diffraction figure of a crystalline powder with an alpha-maltose content of 55.6%.
Figure 3:
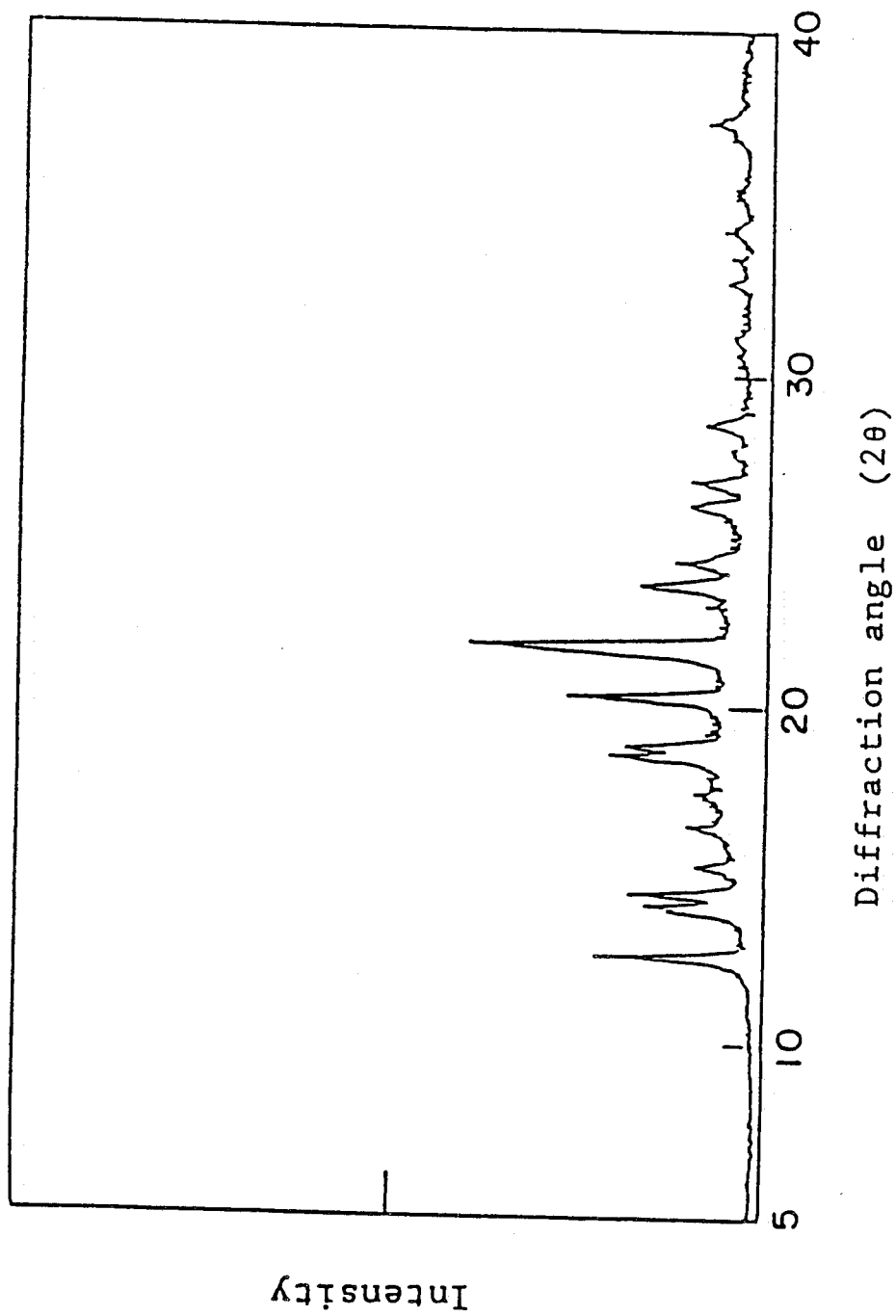
FIG. 3 is the x-ray diffraction figure of a crystalline powder with an alpha-maltose content of 61.4%.
Figure 4:
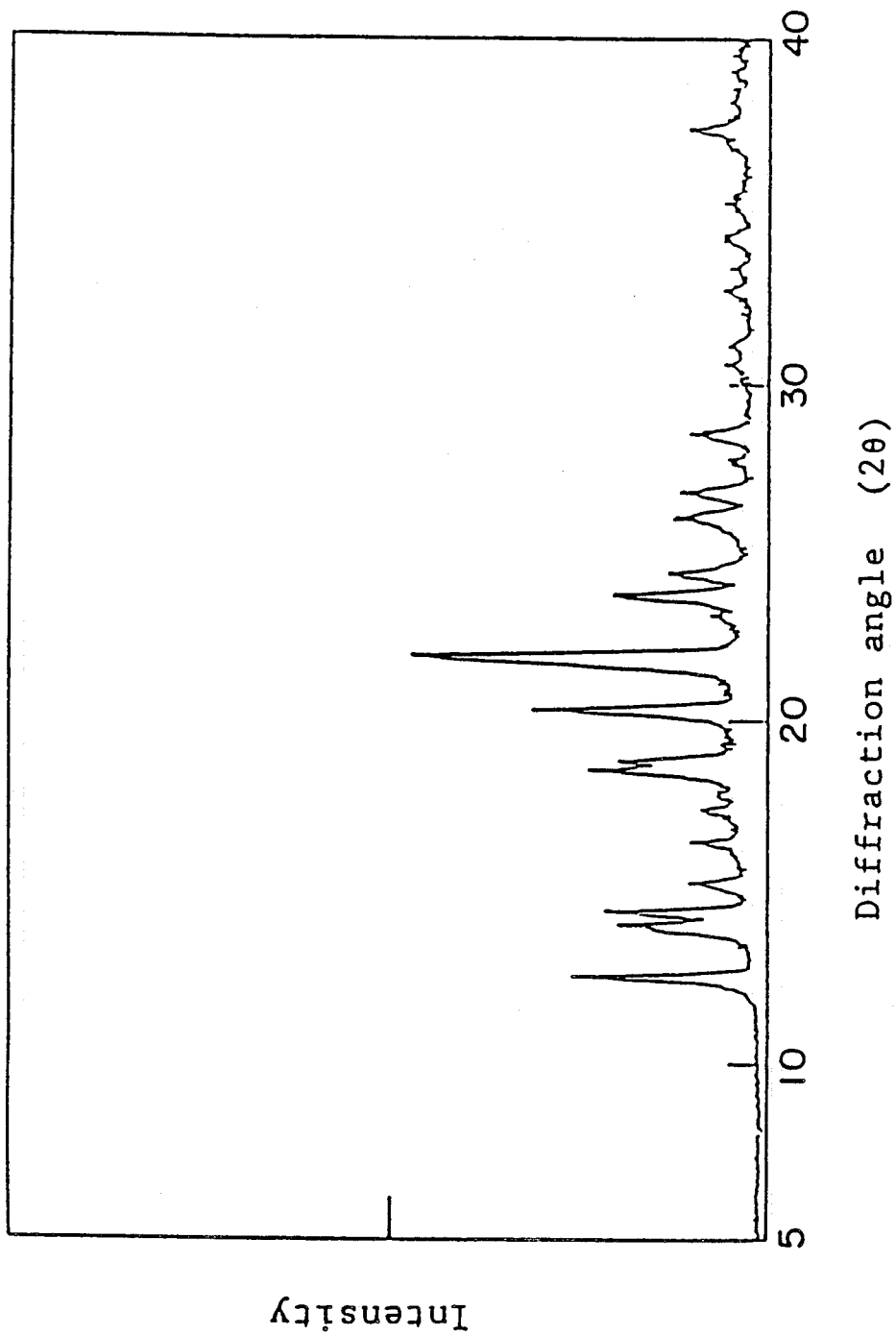
FIG. 4 is the x-ray diffraction figure of a crystalline powder with an alpha-maltose content of 68.7%.
Figure 5:
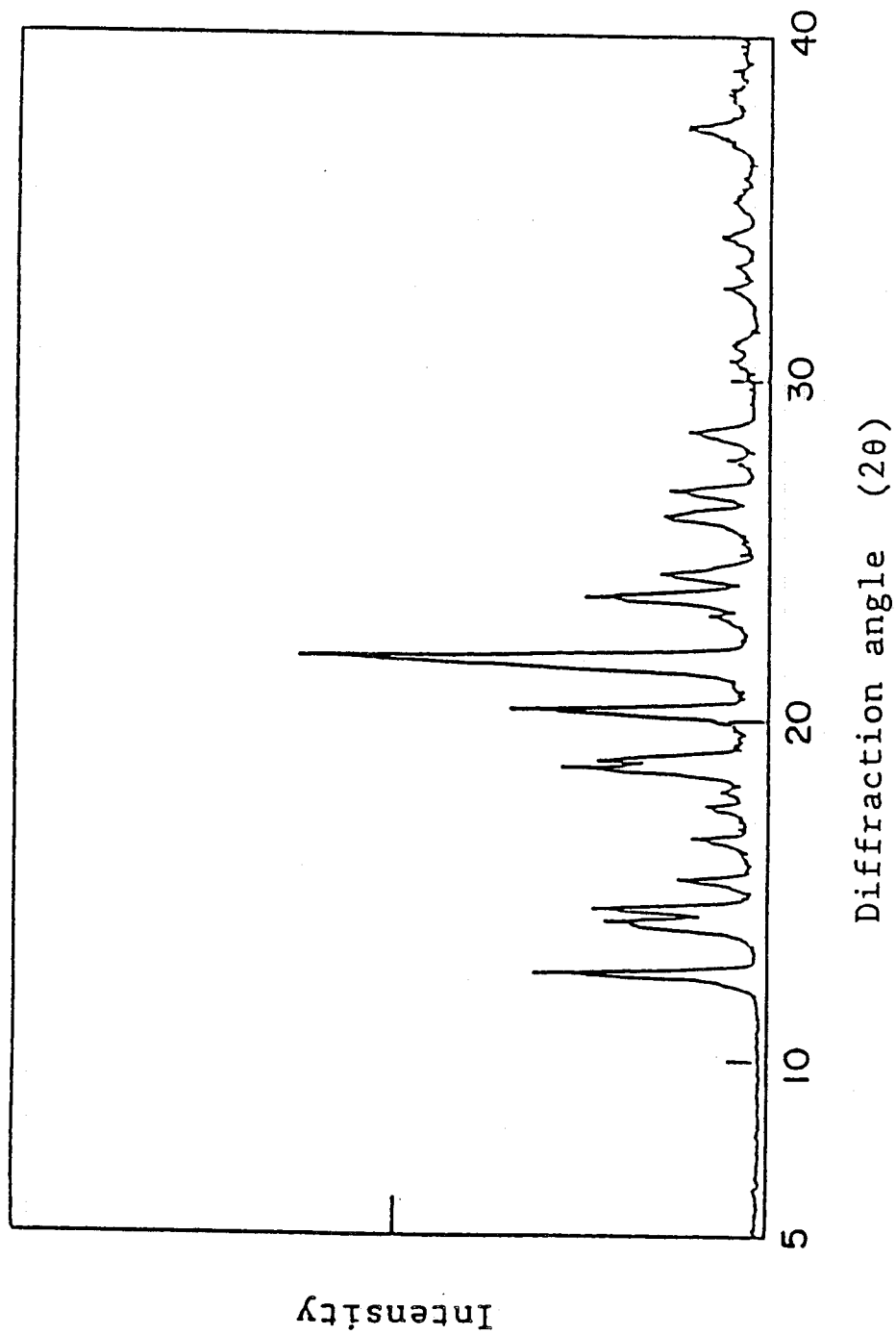
FIG. 5 is the x-ray diffraction figure of a crystalline powder with an alpha-maltose content of 74.2%.

The resultant syrup with a moisture content of about 4.5 w/w % was placed in a crystallizer, added with 2% crystalline alpha-maltose as the seed which had been crystallized and recovered from an about 50 w/v % hot aqueous alcoholic solution of "MALTOSE HHH (a commercialized crystalline high-purity betamaltose hydrate)", and crystallized at 120° C. for 20 minutes. Thereafter, the content was placed in an aluminium tray and aged at 90° C. for 16 hours. The resultant block was cooled to ambient temperature and finely divided. The alpha-maltose isomer content in the resultant powder was determined by gas-chromatography as described by C. C. Sweeley et al., in *Journal of the American Chemical Society*, Vol. 85, pp. 2497–2507 (1963). Separately, the powder was subjected to x-ray diffraction analysis using CuKα ray as described by F. H. Stodola et al., in *Journal of the American Chemical Society*, Vol. 78, pp. 2514–2518 (1956) in order to check the presence of crystal. The employed x-ray diffractometer was "GEIGERFLEX RAD-II B", commercialized by Rigaku Corporation, Chiyoda-ku, Tokyo, Japan. The results were as shown in Table I. The x-ray diffraction figures were as shown in FIGS. 1–6. FIG. 1 is the x-ray diffraction figure of an amorphous powder with an alpha-maltose content of 48.0%; FIG. 2, the x-ray diffraction figure of a crystalline powder with an alpha-maltose content of 55.6%; FIG. 3, an x-ray diffraction figure of a crystalline powder with an alpha-maltose content of 61.4%; FIG. 4, an x-ray diffraction figure of a crystalline powder with an alpha-maltose content of 68.7%; FIG. 5, an x-ray diffraction figure of a crystalline powder with an alpha-maltose content of 74.2%, and FIG. 6, the x-ray diffraction figure of an anhydrous crystalline beta-maltose. The anhydrous amorphous maltose powder gave a similar x-ray diffraction figure as shown in FIG. 1. As the control, the x-ray diffraction study of "MALTOSE HHH" gave a figure as shown in FIG. 7.

These x-ray diffraction results evidently confirm that the alpha-maltose isomer content required for crystallization is 55% or higher, and that the maltose content of a feasible material maltose is 85% or higher.

EXPERIMENT 2

Comparison of several saccharides on dehydrating activity

One variety of anhydrous glucose, sucrose, anhydrous saccharides prepared in Test No. 1–8 in Experiment 1, and material crystalline beta-maltose hydrate of Test No. 5 in Experiment 1 was pulverized to give a particle size of about 100–150 microns, thereafter 1 g of either powder was placed in a plastic Petri dish, diameter of 5 cm, and allowed to stand at 25° C. and a relative humidity of 70%. In the course of the standing, each powder was successively sampled and then measured for moisture content (%). The dehydrating activities of the saccharides were estimated with the moisture contents.

The results were as shown in Table II.

TABLE I

| Test No. | Material maltose (Trade name) | Maltose content (%) | Alpha-maltose isomer content (%) | x-Ray diffraction Crystal | Diffraction figure |
|---|---|---|---|---|---|
| 1 | MALSTAR ® | 68.4 | 48.0 | Anhydrous amorphous oligosaccharide | FIG. 1 |
| 2 | HM-75 | 79.6 | 48.0 | Anhydrous amorphous | FIG. 1 |

TABLE I-continued

Figure 6:
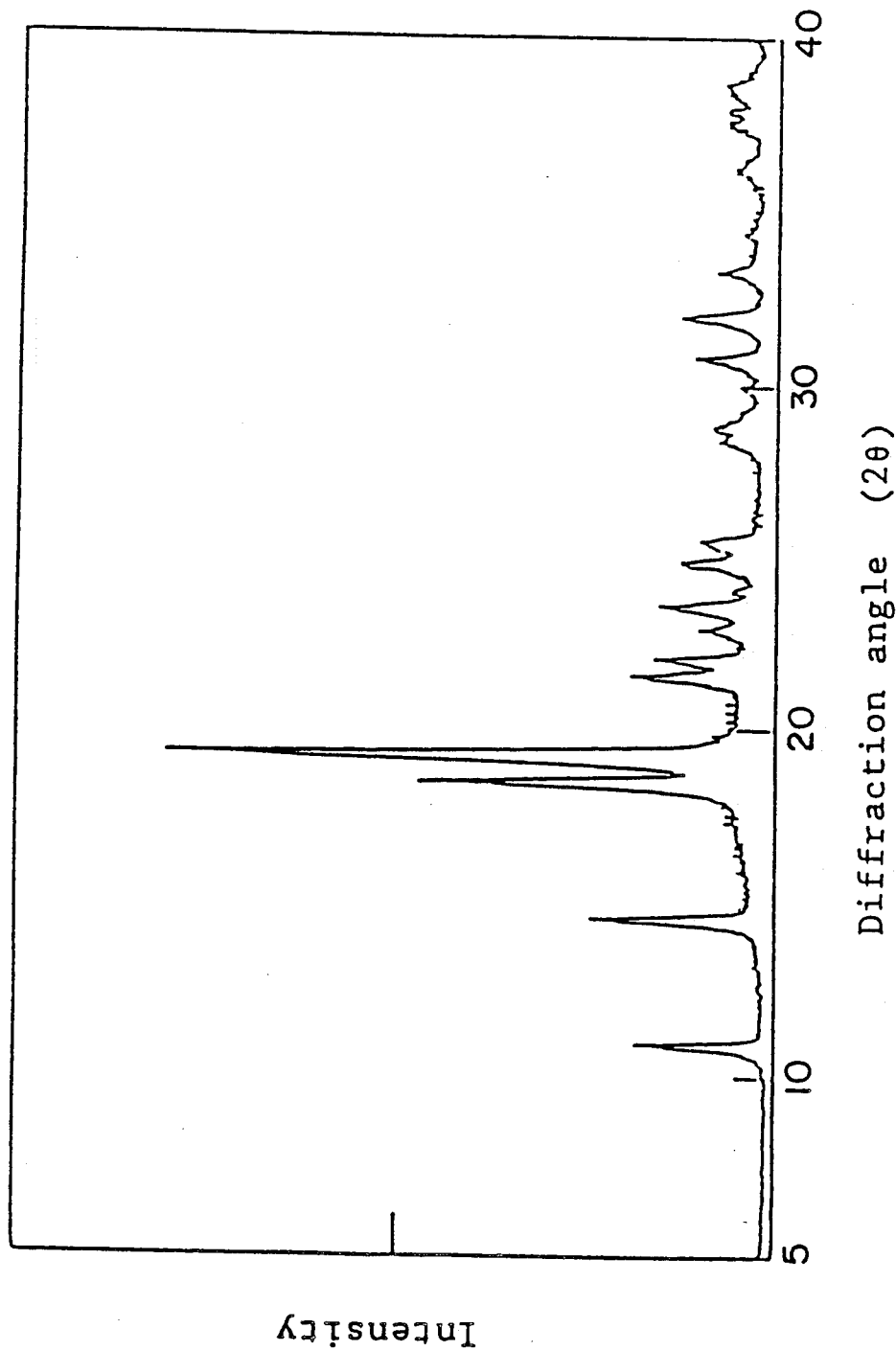
FIG. 6 is the x-ray diffraction figure of an anhydrous crystalline beta-maltose powder.
Figure 7:
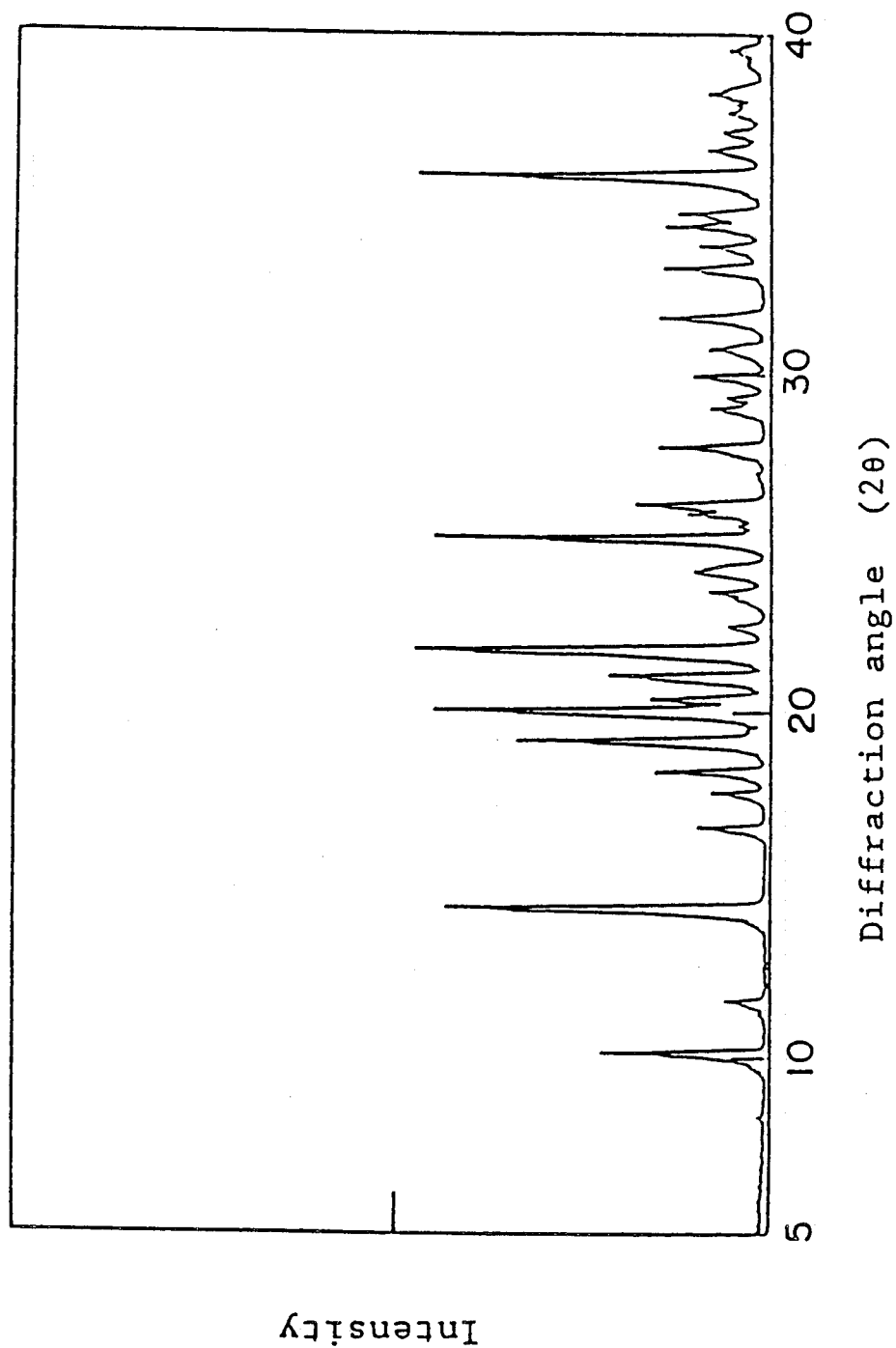
FIG. 7 is the x-ray diffraction figure of a crystalline beta-maltose hydrate powder ("MALTOSE HHH").

| Test No. | Material maltose (Trade name) | Maltose content (%) | Alpha-maltose isomer content (%) | x-Ray diffraction Crystal | Diffraction figure |
| --- | --- | --- | --- | --- | --- |
| 3 | SUNMALT ® | 85.8 | 55.6 | oligosaccharide Anhydrous crystalline alpha-maltose | FIG. 2 |
| 4 | MALTOSE H | 91.5 | 61.4 | Anhydrous crystalline alpha-maltose | FIG. 3 |
| 5 | MALTOSE HH | 96.2 | 68.7 | Anhydrous crystalline alpha-maltose | FIG. 4 |
| 6 | MALTOSE HHH | 99.7 | 74.2 | Anhydrous crystalline alpha-maltose | FIG. 5 |
| 7 | MALTOSE HHH | 99.7 | 48.0 | Anhydrous amorphous maltose | FIG. 1 |
| 8 | MALTOSE HHH | 99.7 | 2.3 | Anhydrous crystalline beta-maltose | FIG. 6 |
| 9 | MALTOSE HHH | 99.7 | 2.3 | Crystalline beta-maltose hydrate | FIG. 7 |

These data confirm that anhydrous maltose with a maltose content of 85% or higher acts as the strong desiccant until it entraps about 5 w/w % of moisture.

On successively determining the x-ray diffraction figure of each sample, no change was noted for anhydrous glucose, sucrose and crystalline beta-maltose hydrate, while the anhydrous maltoses in Test Nos. 3–8 changed with moisture-intake and is, with about 5 w/w % of moisture, converted into crystalline beta-maltose hydrate reaching the equilibrium and changing no more.

Similarly, the anhydrous maltose prepared in Test No. 5 in Experiment 1 was allowed to stand at a regulated relative humidity of 92% and successively measured for moisture content (%). This confirms that even after conversion into crystalline beta-maltose hydrate by entrapping about 5 w/w % moisture the resultant crystalline beta-maltose hydrate still entraps moisture and reaches the equilibrium with a moisture of about 18%. At this time, the resultant product retained its pulverulent form and was neither damp nor flowing.

We found that due to this property anhydrous maltose can be advantageously used as the desiccant for foods, pharmaceuticals, cosmetics, and their materials and intermediates.

EXPERIMENT 3

Use of several saccharides in cream filling

Several saccharides were compared for dehydrating activity when used in cream filling for sandwich cookie.

TABLE II

| Saccharide | Time (hour) 0 | 2 | 4 | 8 | 24 | 72 | Remark |
| --- | --- | --- | --- | --- | --- | --- | --- |
| Anhydrous glucose | 0.30 | 0.43 | 0.42 | 0.44 | 0.46 | 0.46 | Control |
| Sucrose | 0.25 | 0.28 | 0.30 | 0.29 | 0.30 | 0.30 | Control |
| Test No. 1 Anhydrous amorphous oligosaccharide | 0.90 | 2.95 | 3.90 | 5.32 | 8.81 | 12.84* | Control |
| Test No. 2 Anhydrous amorphous oligosaccharide | 0.83 | 2.82 | 3.73 | 5.16 | 8.85 | 12.26* | Control |
| Test No. 3 Anhydrous crystalline alpha-maltose | 0.35 | 2.66 | 3.05 | 4.21 | 5.54 | 5.55 | Present invention |
| Test No. 4 Anhydrous crystalline alpha-maltose | 0.31 | 2.24 | 2.92 | 4.05 | 5.40 | 5.40 | Present invention |
| Test No. 5 Anhydrous crystalline alpha-maltose | 0.30 | 2.01 | 2.84 | 3.93 | 5.37 | 5.37 | Present invention |
| Test No. 6 Anhydrous crystalline alpha-maltose | 0.30 | 2.00 | 2.83 | 3.92 | 5.34 | 5.34 | Present invention |
| Test No. 7 Anhydrous amorphous alpha-maltose | 0.34 | 2.94 | 3.80 | 4.56 | 5.32 | 5.32 | Present invention |
| Test No. 8 Anhydrous crystalline beta-maltose | 0.36 | 2.66 | 3.58 | 4.35 | 5.32 | 5.33 | Present invention |
| Test No. 9 Crystalline beta-maltose hydrate | 5.29 | 5.30 | 5.30 | 5.35 | 5.36 | 5.37 | Control |

Note: (*)means that absorption of the moisture gave a pasty product.

The saccharides tested were anhydrous glucose, sucrose, anhydrous crystalline alpha-maltose prepared in Test No. 5 of Experiment 1 and material crystalline beta-maltose hydrate.

Cream filling was prepared by placing 425 g of shortening in a mixer, admixing the shortening with 500 g of either saccharide, adding thereto a melted fluid of 25 g of soybean oil and 50 g of cacao butter, and whipping the resultant mixture.

The use of crystalline beta-maltose hydrate gave no cream filling because a satisfactory mixing could not be attained.

The obtained cream filling was then allowed to stand under vigorous conditions, i.e. at 29° C. and at a regulated relative humidity of about 92%, and successively measured for moisture content (%) while monitoring its appearance.

The results were as shown in Table III.

These data confirm that the cream filling prepared with anhydrous maltose retains its shape under the vigorous conditions, i.e. at a regulated relative humidity of 92% and at a temperature 29° C., as well as that the anhydrous maltose in the cream filling is converted into crystalline beta-maltose hydrate and then stabilized at the equilibrium with the ambient atmosphere. Also is confirmed that, because of these properties, the moisture in the moistureproof package is entrapped by the cream filling by sandwiching it between, for example, cookies or biscuits, and storing the resultant in the moisture-proof package thereby to effect dehydration and decrease of the relative humidity in the moistureproof package, as well as that the cream filling is stably stored without causing alteration or deterioration over a long period time.

TABLE III

| Saccharide | Standing period (days) | | | |
|---|---|---|---|---|
| | 0 | 8 | 18 | 36 |
| Anhydrous glucose | 0.2% | 5.3%* | 10.2%* | 20.1%* |
| Sucrose | 0.1% | 5.7%* | 10.6%* | 20.6%* |
| Anhydrous crystalline alpha-maltose | 0.2% | 5.4%** | 5.2%** | 5.3%** |
| Crystalline beta-maltose hydrate | Gave no cream filling | | | |

Note: (*)means that the oil separated and became sticky; and (**), the cream filling was stable and slightly hard.

EXPERIMENT 4

Comparison of several saccharides for effects on gelatinized starch

Four hundred grams of waxy rice powder was dissolved in 600 ml of water, and the resultant was poured onto a wet cloth extended over a wooden frame and steamed at 105° C. for 10 minutes to obtain a gelatinized starch.

The gelatinized starch was then admixed in a mixer with 800 g of either anhydrous crystalline alpha-maltose prepared in Test No. 5 in Experiment 1 or crystalline beta-maltose hydrate. When the mixture attained homogeneity, it was added with 200 g of corn starch, sufficiently kneaded, shaped and dried briefly for 2 hours in a stream of 40° C. air to obtain "gyuhi".

Upon standing at ambient temperature (25° C.) in an open system, the "gyuhi" product using crystalline beta-maltose hydrate showed a growth of bread mold after a lapse of 12 days, while the product using anhydrous maltose had no microbial contamination even after a lapse of 20 days.

On the twentieth day, the "gyuhi" products were cut and their sections were observed. As the result, the "gyuhi" product using anhydrous maltose slightly hardened and crystallized at its outer layer but it had a semi-transparent inner part with such a fresh satisfactory gloss and viscosity as immediately on its preparation. The x-ray diffraction figure of the crystal appearing at the outer layer of the "gyuhi" product confirmed that the anhydrous maltose used was converted completely into crystalline beta-maltose hydrate.

The "gyuhi" product using crystalline beta-maltose hydrate showed a growth of mold at the outer layer, and its whole sectional layer was cloudy and glossless.

Thus, it was found that anhydrous maltose acts as the desiccant for gelatinized starch, as well as preventing microbial contamination and retrogradation of gelatinized starch.

This property is utilizable in various products that use gelatinized starch such as "gyuhi" and flour paste.

The following explains the production of anhydrous maltose powder.

EXAMPLE FOR REFERENCE 1

A suspension of 1 part of potato starch and 10 parts of water was added with a commercialized liquefying bacterial alpha-amylase, gelatinized by heating to 90° C., and immediately heated to 130° C. to suspend the enzymatic reaction. Thus, a liquefied starch solution with a Dextrose Equivalent (DE) of about 0.5 was obtained. The starch solution was immediately cooled to 55° C., added with 100 units/g starch of isoamylase (EC 3.2.1.68) derived from a culture of *Pseudomonas amyloderamosa* ATCC 21262, and 50 units/starch of a soybean beta-amylase (EC 3.2.1.2), commercialized by Nagase & Company, Ltd., Osaka, Japan, under the trade name of "#1500", and saccharified at pH 5.0 for 40 hours to obtain a high-purity maltose solution with a maltose content of 92.5%, which was then decolored with activated carbon, followed by purification and deionization with ion exchange resins. The maltose solution was then concentrated to 75%, fed to a crystallizer, added with 1% crystalline beta-maltose monohydrate seed, adjusted to 40° C., and gradually cooled to 30° C. in 2 days under gentle stirring conditions to obtain a massecuite. The crystals were separated from the massecuite with a basket-type centrifuge, and washed by spraying a small amount of water to obtain a crystalline high-purity beta-maltose hydrate (purity 99.0%).

The high-purity maltose thus obtained was dissolved with a small amount of water by heating, charged in an evaporator, and evaporated in vacuo to prepare a syrup with a moisture content of 5.5 w/w %. The content was fed to a crystallizer, added with 1% crystalline alpha-maltose seed obtained by the method in Test No. 6 in Experiment 1, crystallized at 100° C. for 5 minutes while stirring, poured into a plastic tray, and aged at 70° C. for 6 hours. The resultant block was then finely divided with a pulverizer, and dehydrated by fluidized-bed drying to obtain a pulverulent crystalline alpha-maltose with an alpha-maltose isomer content of 73.3% and a moisture content of 0.42 w/w % in the yield of about 92% based on the material crystalline high-purity beta-maltose hydrate.

The product can be advantageously used as the desiccant for hydrous matters such as foods, pharmaceutical, cosmetics, and their materials and intermediates, as well as a white powder sweetener with a mild sweetness.

EXAMPLE FOR REFERENCE 2

An aqueous solution of a high-purity maltose with a maltose content of 92.5%, prepared by the method in Example for reference 1, was concentrated in vacuo to give a moisture content of 20 w/w %, and sprayed through a nozzle, equipped at the top of a spraying tower, with a high-pressure pump. Simultaneously, 100° C. air was passed from the top of the tower towards a net conveyer carrying a fluidized crystalline alpha-maltose as the seed crystal, placed at the bottom of the tower, to collect the pulverized product on the net conveyer and also to fluidize the product out of the tower over a period of 60 minutes while passing a stream of 70° C. air upwards through the net. The resultant product was then placed in an ageing tower and aged for 4 hours in a stream of 70° C. air to obtain a crystalline alpha-maltose powder with an alpha-maltose content of 66.2% and a moisture content of 0.55 w/w % in the yield of about 94% based on the material high-purity maltose.

Like the anhydrous maltose powder in Example for Reference 1, the product can be advantageously used as the desiccant for various hydrous matters, as well as sweetener.

EXAMPLE FOR REFERENCE 3

A suspension of 2 parts of corn starch and 10 parts of water was added with a commercialized bacterial liquefying alpha-amylase, gelatinized by heating to 90° C., and heated to 130° C. to suspend the enzymatic reaction in order to prepare a liquefied starch solution with a DE of about 2. The starch solution was immediately cooled to 55° C., added with 120 units/g starch of isoamylase (EC 3.2.1.68), prepared from a culture of Pseudomonas amyloderamosa ATCC 21262, and 30 units/g starch of a soybean beta-amylase, saccharified at pH 5.0 for 40 hours, and purified similarly as in Example for Reference 1 to obtain a high-purity maltose solution with a maltose content of 88.6%, which was then concentrated in vacuo into a syrup with a moisture content of 3.5 w/w %.

The syrup was then transferred into a crystallizer, added with 2.5% crystalline alpha-maltose seed obtained by the method in Example for Reference 2, crystallized at 120° C. for 10 minutes while stirring, poured into an aluminium tray, and aged at 70° C. for 18 hours to obtain a solid. Similarly as in Example for Reference 1, the solid was divided and dehydrated to obtain a crystalline alpha-maltose powder with an alpha-maltose isomer content of 63.9% and a moisture content of 0.60 w/w % in the yield of about 94% based on the material high-purity maltose.

Like the anhydrous maltose powder in Example for Reference 1, the product can be advantageously used as the desiccant for various hydrous matters, as well as sweetener.

EXAMPLE FOR REFERENCE 4

A 45 w/w % aqueous solution of "HM-75", a starch sugar solution with a maltose content of 79.6%, commercialized by Hayashibara Co., Ltd., Okayama, Japan, was used as the feed solution. "XT-1022 E (Na+)", a strongly-acidic cation exchange resin, commercialized by Tokyo Chemical Industries, Kita-ku, Tokyo, Japan, was chosen and packed in water suspension in four 5.4 cm jacketed stainless steel columns to give respective bed depth of 5 m. The columns were cascaded to give a total bed depth of 20 m.

The feed solution was admitted into the columns in an amount of 5 v/v % to the bed volume, and fractionated by passing 55° C. water at a space velocity of 0.13 through the columns while keeping the inner temperature of the column at 55° C. to obtain effluents. The maltose-rich fraction was separated from the effluents to obtain a high-purity maltose solution with a maltose content of 94.4%.

After repeating these operations 20 cycles, the resultant high-purity maltose solutions were pooled and concentrated in vacuo to obtain a syrup with a moisture content of 4.0 w/w %, which was then transferred into a crystallizer, added with 2% crystalline alpha-maltose seed obtained by the method in Example for Reference 2, crystallized at 110° C. for 20 minutes under stirring, and granulated with a screw-type extrusion granulator. The resultant product was then placed in a drying chamber and aged therein by dehydration in a stream of 80° C. air for 2 hours to obtain a crystalline alpha-maltose powder with an alpha-maltose isomer content of 69.2% and a moisture content of 0.48 w/w % in the yield of about 93% based on the material high-purity maltose.

Like the anhydrous maltose powder in Example for Reference 1, the product can be advantageously used as the desiccant for various hydrous matter, as well as sweetener.

EXAMPLE FOR REFERENCE 5

A crystalline beta-maltose hydrate obtained by the method in Example for Reference 1 was lyophilized at 95° C. for 2 days to prepare an anhydrous crystalline beta-maltose powder with a moisture content of 0.36 w/w %.

Like the anhydrous maltose powder in Example for Reference 1, the product can be advantageously used as the desiccant for hydrous matters, as well as sweetener.

EXAMPLE FOR REFERENCE 6

An aqueous solution of a high-purity maltose obtained by the method in Example for Reference 3 was concentrated in vacuo, and sprayed from a nozzle provided at the upper part of a spray-drying tower with a high pressure pump through a stream of 160° C. air towards the bottom of the spray-drying tower to effect dehydration. Simultaneously, the sprayed product was collected at the bottom of the spray-drying tower, and conveyed outside the tower to obtain a powder with a moisture content of 0.40 w/w %. The powder was then mixed with about 0.1% of a crystalline beta-maltose hydrate seed obtained by the method in Example for Reference 1 to obtain a substantially-amorphous anhydrous maltose powder.

Like the anhydrous maltose powder in Example for Reference 1, the product can be advantageously used as the desiccant for hydrous matter, as well as sweetener.

EXAMPLE FOR REFERENCE 7

An aqueous solution of a high-purity maltose obtained by the method in Example for Reference 4 was concentrated in vacuo and then spray-dried similarly as in Example for Reference 6 to obtain an anhydrous amorphous maltose powder with a moisture content of 0.45 w/w %.

Like the anhydrous maltose obtained in Example for Reference 1, the product can be advantageously used as the desiccant for hydrous matters, as well as sweetener.

Several embodiments and features of the present invention will hereinafter be described.

EXAMPLE 1

Desiccant

Twenty gram aliquots of an anhydrous maltose powder obtained by the method in Example for Reference 5 were packed in small moisture-permeable paper bags.

The product can be advantageously used as the desiccant for moistureproof package containing a dehydrated food such as "ajitsuke-nori" or cookie.

The product stably stores dehydrated- or oily-foods in conjunction with conventional deoxygenator.

EXAMPLE 2

"Oboro-fu gyuhi"

Four kilograms of waxy rice powder was dissolved in 6,000 ml of water, and the resultant was poured into a wet cloth extended over a wooden frame and steamed at 100° C. for 20 minutes. The resultant product was kneaded with 8 kg of an anhydrous maltose powder obtained by the method in Example for Reference 7 and 1 kg of sucrose, added with 1 kg of corn syrup, sufficiently kneaded, shaped and allowed to stand under ambient conditions for 6 hours to convert the anhydrous maltose into crystalline beta-maltose hydrate at the outer layer of the resultant product. Thereafter, the product was subjected briefly to roll crusher to crack the surface.

The product excellent in taste and flavor and scarcely susceptive to microbial contamination retains its high-quality over a long period of time.

EXAMPLE 3

"Imo-gashi (a snack food prepared from sweet potato)"

Sweet potatoes were cut into slices about 1 cm thick, steamed, cooled by standing, and dehydrated by coating with an anhydrous maltose powder obtained by the method in Example for Reference 1 to convert the anhydrous maltose into crystalline beta-maltose hydrate to obtain "imo-gashi" where the beta-maltose hydrate was attached on the surface.

The product was a tasty and stable "imo-gashi".

EXAMPLE 4

Fondant containing mayonnaise

Five kilograms of mayonnaise was admixed with 5 kg of an anhydrous maltose powder obtained by the method in Example for Reference 5 to convert the anhydrous maltose into crystalline beta-maltose hydrate.

The product can be advantageously used in confectioneries.

The chilled product with a mayonnaise flavor is suitable for frozen dessert.

EXAMPLE 5

French dressing powder

Two kilograms of French dressing was mixed with 8 kg of an anhydrous maltose powder obtained by the method in Example for Reference 3 while stirring, transferred into a tray, and blocked by 2-day standing to convert the anhydrous maltose into crystalline beta-maltose hydrate.

The block was then pulverized with a scraper and sieved to obtain a French dressing powder excellent in taste and flavor.

The product can be advantageously used for sprinkling on vegetable salad, as well as for seasoning fresh vegetables for sandwich.

EXAMPLE 6

Brandy powder

Ten g of pullulan was dissolved in 2,000 ml of brandy, and the resultant solution was mixed with 10 kg of an anhydrous maltose powder obtained by the method in Example for Reference 6, blocked and pulverized similarly as in Example 5 to obtained a brandy powder.

Since during conversion into crystalline beta-maltose hydrate the anhydrous maltose swelled to increase its volume a little over 2-folds, the resultant block with a decreased hardness was pulverized easily.

The product is a powder flavor that exhibits in the mouth an appropriate sweetness and a satisfactory brandy flavor.

The product can be advantageously used for flavoring tea, as well as preparing confectioneries such as premixes and candies.

The product can be advantageously shaped with granulator or tabletting machine, prior to its use.

EXAMPLE 7

"Miso" powder

One kilograms of "aka-miso (a soybean paste with a red appearance)" was mixed with 3 kg of an anhydrous maltose powder obtained in Example for Reference 2, poured into wells provided on a metal plate, solidified by allowing at ambient temperature overnight and removed from the wells to obtain "miso" solids, about 4 kg each, which were then subjected to a pulverizer to obtain a "miso" powder.

The product can be advantageously used as the seasoning for instant Chinese noodle and instant "miso" soup.

In addition, the product is usable in confectioneries.

EXAMPLE 8

Soy sauce powder

One part of "usukuchi-shoyu (a soy sauce with a relatively thin taste)" was sprayed onto a mixture of 4 parts of an anhydrous maltose powder obtained by the method in Example for Reference 7 and 0.02 parts of a commercialized crystalline beta-maltose hydrate fluidizing on a conveyer, after which the resultant product was conveyed outside towards an ageing tower and allowed to stand in the tower at 30° C. overnight to convert the anhydrous maltose into crystalline beta-maltose hydrate.

The product can be advantageously used as the seasoning for instant Chinese noodle and instant soup.

EXAMPLE 9

Yolk powder

A yolk prepared with fresh eggs was pasteurized at 60–64° C. with a plate-type heat-pasteurizer, and one part of the obtained yolk fluid was added with 4 parts of an anhydrous maltose powder obtained by the method in Example for Reference 6, blocked and pulverized similarly as in Example 5 to obtain a yolk powder.

The product can be advantageously used in premixes, frozen desserts and emulsifiers, as well as in baby food and nutritious diet such as liquid food for peroral- or parenteraladministration.

Also, the product can be advantageously used in skin treatment and hair tonic.

EXAMPLE 10

Butter powder

Ten kilograms of butter was mixed with 20 kg of an anhydrous maltose powder obtained by the method in Example for Reference 2 with a mixer, blocked and pulverized similarly as in Example 5 to obtain a butter powder.

The product can be advantageously used in premix, potage soup, stew and "chahan (a Chinese fried rice)", as well as in nutritious diet such as intubation feeding.

EXAMPLE 11

Cream powder

Two kilograms of fresh cream was mixed with 8 kg of an anhydrous maltose powder obtained by the method in Example for Reference 3, blocked and pulverized similarly as in Example 5 to obtain a cream powder.

The cream powder excellent in taste and flavor can be advantageously used for seasoning coffee and tea, as well as preparing premix, frozen dessert, cake, candy and nutritious diet such as intubation feeding.

Also, the product can be advantageously used in skin treatment and hair tonic.

EXAMPLE 12

Yogurt powder

Two kg of plane yogurt was mixed with 10 kg of an anhydrous maltose powder obtained by the method in Example for Reference 4, blocked and pulverized similarly as in Example 5 to obtain a yogurt powder.

The product excellent in taste and flavor stably retains the lactic acid bacteria over a long period of time. The product can be advantageously used to prepare premix, frozen dessert, margarine, whipped cream, spread, cheese cake and jelly with a yogurt flavor, as well as to prepare nutritious diet such as intubation feeding.

The biochemicals obtained by shaping the product with granulator or tabletting machine can be advantageously used as the medicine for intestinal disorders.

EXAMPLE 13

Hot cake mix

Two hundred grams of flour was mixed with 60 g of a yolk powder obtained by the method in Example 9, 78 g of a butter powder obtained by the method in Example 10, 10 g of sucrose, 12 g of baking powder and 0.5 g of salt to obtain a hot cake mix.

A tasty hot cake can be easily prepared by dissolving the product in water or milk, and baking the resultant mixture.

EXAMPLE 14

Ginseng extract powder

Five hundred grams of ginseng extract was kneaded with 1.5 kg of an anhydrous maltose powder obtained by the method in Example for Reference 6, blocked and pulverized similarly as in Example 5.

The resultant powder was then fed to a granulator together with appropriate amounts of vitamin $B_1$ and vitamin $B_2$ powders to obtain a ginseng granule containing vitamins.

The product can be advantageously used as tonic and medicine for restoring fatigue.

EXAMPLE 15

Solid composition for fluid food

Twenty-five gram aliquots of a composition consisting of 500 part of an anhydrous maltose powder obtained by the method in Example for Reference 1, 270 parts of a yolk powder obtained by the method in Example 9, 209 parts of defatted milk, 4.4 parts of sodium chloride, 1.85 parts of potassium chloride, 4 parts of magnesium sulfate, 0.01 part of thiamine, 0.1 part of sodium ascorbate, 0.6 parts of vitamin E acetate, and 0.04 parts of nicotinamide were packed in small moistureproof laminated bags, followed by heat-sealing.

The composition decreases the moisture in the bag and requires no low-temperature storage because it is stable over a long period of time even at ambient temperature.

The product is excellent in dispersibility and solubility in water.

A bag of the product, dissolved in 150–300 ml of water, can be used as the liquid food in peroral- or parenteral-administration through the nasal cavity, stomach or intestine.

EXAMPLE 16

Solid injection

Newborn hamsters were injected with antiserum prepared in conventional manner to weaken their immunoreaction, implanted subcutaneously with BALL-1 cell and fed in usual manner for 3 weeks. The tumor masses, formed subcutaneously in the body of the hamsters, were extracted, minced and disaggregated in saline. The cell thus obtained was washed with serum-free RPMI 1640 medium (pH 7.2), suspended in a fresh preparation of the same culture medium to give a cell density of about $2 \times 10^6$ cells/ml, and incubated at 35° C. The culture medium was added with 200 U/ml of an interferon preparation, incubated at this temperature for an additional 2 hours, added with Sendai virus in an amount of about 300 hemagglutination titer/ml, and incubated for an additional 20 hours to induce interferon production. The resultant culture was then centrifuged at about $1,000 \times g$ to remove the sediment, and the supernatant was filtered with a membrane filter The filtrate was passed through a column of immobilized anti-interferon antibody in conventional manner, and the non-adsorbed part was removed. The adsorbed part was then eluted and concentrated with a membrane to obtain a liquid preparation, concentration of about 0.01 w/v %, specific activity of about $1.5 \times 10^8$ U/mg protein, in the yield of about 4 ml per hamster.

Eight gram aliquots of a pyrogen-free anhydrous maltose powder obtained by the method in Example for Reference 5 were placed in 100 ml moistureproof plastic bottles which were then added with 0.2 ml aliquot of the liquid interferon preparation (about $3 \times 10^6$ U), rubber-stopped and cap-sealed under sterile conditions to obtain a solid injection.

This process has the advantages that it does not require treatment, apparatus and energy for lyophilization because the solution containing interferon is dehydrated only by dropping it onto a portion of anhydrous maltose powder and effectively stabilized by the maltose.

Since the product is readily dissolvable in water, it can be advantageously used as the test reagent, antiviral agent or antioncotic for subcutaneous, intramascular or intravenous injection.

The titer of human interferon was assayed by the conventional plaque reduction method, and the hemagglutination titer was measured by the method as reported by J. E. Salk, *The Journal of Immunology*, Vol. 49, pp. 87–98 (1944).

EXAMPLE 17

Solid injection

Newborn hamsters were injected with an antiserum prepared from rabbit in conVentional manner to weaken their immunoreaction, implanted subcutaneously with an established SV-40 virus-transformed human monocytic cell fed in usual manner for one week, injected intraperitoneally with $10^7$ viable BCG cells and fed for an additional 2 weeks. The tumor masses, formed subcutaneously in the body of the hamsters, about 15 g each, were extracted, minced and disaggregated by suspending in saline containing trypsin. The obtained cell Was washed with Eagle's minimal essential medium (pH 7.2), supplemented with 5 v/v % human serum, diluted with a fresh preparation of the same culture medium, prewarmed to 37° C., to give a cell density of about $5 \times 10^6$ cells/ml, added with about 10 micrograms/ml of *E. coli* endotoxin, and incubated at this temperature for 16 hours to induce tumor necrosis factor production.

The resultant culture was then centrifuged at about $1,000 \times g$ and 4° C. to remove the sediment, and the supernatant was dialyzed against saline containing 0.01M phosphate buffer (pH 7.2) for 21 hours, filtered with a membrane filter, concentrated and lyophilized to obtain a powder possessing tumor necrosis factor activity. The obtained powder was then purified with adsorption and desorption using ion exchange, molecular weight fractionation using gel filtration, concentration and filtration using membrane filter in accordance with the method as reported in G. Bodo, *Symposium on Preparation, Standardization and Clinical Use of Interferon,* 11th International Immunobiological Symposium 8 & 9, June 1977, Zagreb, Yugoslavia, to remove the interferon, and the resultant interferon-free product was purified with salting-out using ammonium sulfate and affinity-chromatography using concanavalin A-bound Sepharose to obtain an about 0.01 w/v % liquid preparation containing tumor necrosis factor in the yield of about 30 ml per hamster. Tumor necrosis factor is characterized in that it effects hemorrhagic cytolysis on Meth A sarcoma but no affects on normal human cells. The tumor necrosis factor obtained in this way was a glycoprotein with a specific activity of about $3.5 \times 10^5$ U/mg protein and free of the inducer used.

Fifty gram aliquots of a pyrogen-free anhydrous maltose powder obtained by the method in Example for Reference 4 were placed in 500 ml glass bottles, added with 0.5 ml of the liquid preparation containing tumor necrosis factor (about $1.75 \times 10^3$ U), rubber-stopped and cap-sealed under sterile conditions to obtain a solid injection.

This process has the advantages that it does not require treatment, equipment and energy for lyophilization because the solution containing tumor necrosis factor is dehydrated by the anhydrous maltose, as well as that it is effective in stabilization of tumor necrosis factor.

Since the product is readily dissolvable in water, it can be advantageously used as the antioncotic, hyperalimentation and injection for instillation.

The titer of tumor necrosis factor was assayed by the method in *Lymphokines*, Vol. 2, pp. 235–272 "Tumor Necrosis Factor" (1981), wherein L-929 cell that is sensitive to tumor necrosis factor is cultured for a prescribed time, followed by counting of the number of the viable cells.

EXAMPLE 18

Ointment for treating trauma

Three grams of iodine in 50 ml methanol was admixed with 500 g of an anhydrous maltose powder obtained by the method in Example for Reference 7, mixed with 200 ml of 10 w/v % aqueous pullulan solution, and allowed to stand at ambient temperature overnight to convert the anhydrous maltose into crystalline beta-maltose hydrate to obtain an ointment with appropriate spreading rate and adhesiveness.

The product can be used for treating trauma such as incised wound, abrasion, burn and trichophytic ulcer by applying it directly onto the trauma surface, or by applying it on gauze or oilpaper which is then placed on the trauma surface.

The deinfectant- and alimentary-activities of the maltose in the product shortens the healing period and heals trauma well.

As described above, the present invention provides a novel desiccant containing anhydrous maltose. The present desiccant can be advantageously used to decrease the atmospheric moisture in a moistureproof package that encloses, for example, dehydrated food, as well as to decrease the moisture content of various hydrous matters, for example, foods, pharmaceuticals, cosmetics, chemicals, and their materials and intermediates.

By the practice of the present method wherein dehydration is effected by converting anhydrous maltose into crystalline beta-maltose hydrate to substantially decrease moisture, a high-quality dehydrated products can be prepared without, as well as using vigorous processing conditions such as heat-drying, deteriorating hydrous matters, for example, foods which tend to loose their flavor, and pharmaceuticals which tend to decompose or inactivate their effective ingredient.

The dehydrated products obtained in this way retain their high-quality over a long period of time because alteration and deterioration such as microbial contamination, hydrolysis, souring and browning are prevented in the product.

While a preferred embodiment of the invention has been described using specific terms, such description is for illustrative purpose only, and it is to be understood that changes and variations may be made without departing from the spirit or scope of the following claims.

We claim:

1. A dehydrated product containing crystalline β-maltose hydrate obtained by the method comprising incorporating anhydrous maltose as a desiccant into a hydrous matter to convert the anhydrous maltose into crystalline betamaltose hydrate, and dehydrating the hydrous matter.

2. The product of claim 1, wherein the maltose content of said anhydrous maltose is 85 w/w % or higher based on the dry solid.

3. The product of claim 1, wherein said anhydrous maltose is in pulverulent form.

4. The product of claim 1, wherein the moisture content of said anhydrous maltose is lower than 3 w/w %.

5. The product of claim 1, wherein 0.01–500 parts by weight of anhydrous maltose is incorporated into one part by weight of said hydrous matter.

6. The product of claim 1, wherein said anhydrous maltose is a member selected from the group consisting of anhydrous crystalline alpha-maltose, anhydrous crystalline beta-maltose, anhydrous amorphous beta-maltose, and mixtures thereof.

7. The product of claim 1, wherein said hydrous matter contains one or more members selected from the group consisting of gelatinized starch, alcohol, oil-soluble substance, and bioactive substance.

8. A food product in accordance with claim 1.

9. A pharmaceutical in accordance with claim 1.

10. A cosmetic in accordance with claim 1.

* * * * *